United States Patent
Hafez et al.

(10) Patent No.: US 11,484,325 B2
(45) Date of Patent: Nov. 1, 2022

(54) PATIENT-SPECIFIC GUIDE FOR REPAIRING THE PELVIC BONE DEFECTS DEPENDING ON BONE QUALITY IN FIXING ARTIFICIAL HIP JOINT SURGERIES

(71) Applicant: Mahmoud. Alm El Din Hafez, Giza (EG)

(72) Inventors: Mahmoud Alm El Din Hafez, Giza (EG); Ahmed Abdel Moghny Salem, Giza (EG)

(73) Assignee: Mahmoud Alm El Din Hafez, Giza (EG)

( * ) Notice: Subject to any disclaimer, the term of this patent is extended or adjusted under 35 U.S.C. 154(b) by 0 days.

(21) Appl. No.: 16/763,717

(22) PCT Filed: Nov. 8, 2018

(86) PCT No.: PCT/EG2018/000029
§ 371 (c)(1),
(2) Date: May 13, 2020

(87) PCT Pub. No.: WO2019/091538
PCT Pub. Date: May 16, 2019

(65) Prior Publication Data
US 2020/0337714 A1    Oct. 29, 2020

(30) Foreign Application Priority Data

Nov. 13, 2017 (EG) .............................. 2017110030
May 13, 2018 (EG) .............................. 2018050804

(51) Int. Cl.
*A61B 17/17* (2006.01)
*A61B 17/56* (2006.01)
(Continued)

(52) U.S. Cl.
CPC .......... *A61B 17/1746* (2013.01); *A61B 17/56* (2013.01); *A61B 17/1735* (2013.01);
(Continued)

(58) Field of Classification Search
CPC . A61B 17/1746; A61B 17/56; A61B 17/1735; A61B 17/15; A61B 2017/568;
(Continued)

(56) References Cited

U.S. PATENT DOCUMENTS

2011/0184419 A1* 7/2011 Meridew ............ A61B 17/1637
606/91
2014/0012266 A1* 1/2014 Bonin, Jr. .......... A61B 17/1778
606/88
(Continued)

FOREIGN PATENT DOCUMENTS

WO      2014089291 A1    6/2014

*Primary Examiner* — Marcela I. Shirsat
(74) *Attorney, Agent, or Firm* — Dickinson Wright PLLC; Andrew D. Dorisio

(57) ABSTRACT

A patient specific guide for hip replacement for patients undergoing hip replacement surgery. The guide works for correction of the acetabulum defects based on a finite element model, which detect the bone quality and guide the surgeons for the optimum screws trajectories. The guide surface reflects the acetabular morphology which provide a correct posting of the cup, especially for the complex case as bone loss, severe fractures and tumors. CT-scan images are used to construct the 3D model of the acetabulum bone, therefore a finite element and virtual surgery planning methods are applied to create the electronic file of the patient specific guide. In final step, the 3D printers are used to produce the patient specific guide.

18 Claims, 6 Drawing Sheets

(51) Int. Cl.
  *B33Y 80/00* (2015.01)
  *A61F 2/46* (2006.01)
  *A61B 34/10* (2016.01)
  *A61F 2/30* (2006.01)

(52) U.S. Cl.
  CPC ... *A61B 2017/568* (2013.01); *A61B 2034/108* (2016.02); *A61F 2/4609* (2013.01); *A61F 2002/30578* (2013.01); *A61F 2002/30948* (2013.01); *A61F 2002/4687* (2013.01); *B33Y 80/00* (2014.12)

(58) Field of Classification Search
  CPC .... A61B 2034/108; A61F 2/34; A61F 2/4609; A61F 2002/30578; A61F 2002/30948; A61F 2002/3401; A61F 2002/4687
  USPC .......................................... 606/91; 623/22.11
  See application file for complete search history.

(56) References Cited

U.S. PATENT DOCUMENTS

| | | | |
|---|---|---|---|
| 2014/0135940 A1* | 5/2014 | Goldstein | A61B 17/15 623/22.21 |
| 2014/0163564 A1 | 6/2014 | Bollinger | |
| 2014/0276870 A1 | 9/2014 | Eash | |
| 2015/0012001 A1 | 1/2015 | Theiss et al. | |

* cited by examiner

PATIENT-SPECIFIC GUIDE FOR REPAIRING THE PELVIC BONE DEFECTS DEPENDING ON BONE QUALITY IN FIXING ARTIFICIAL HIP JOINT SURGERIES

This application claims the benefit of Egyptian Provisional application No. 30/2017 filed on Nov. 13, 2017 and Egyptian Patent Application No. 804/2018 on May 13, 2018.

TECHNICAL FIELD

This invention relates to a patient specific guides for hip replacement for patients who going to hip replacement surgery.

PRIOR ART

Fixing artificial hip joints surgeries are performed with a plurality of traditional medical tools. Hip joint, especially the acetabulum, is innate in the body and hence it is almost unseen. Therefore, performing artificial pelvic joint fixation surgeries requires accurate surgical planning by a skillful and experienced surgeon. Many surgeons depend on patient-specific guides (templates) for specifying the position and path of fastening screws of the pelvic bone acetabulum. The currently available guide is the three-cylinder fixation guide. The cylinders are connected to a central cylinder for making one central opening of five or six openings required for fixing the artificial hip joint acetabulum.

DISADVANTAGES OF PRIOR ART

Performing surgeries using traditional tools is inefficient; in particular preparing the pelvic joint acetabulum that is innate in the body and seen. It is difficult to determine bone quality and thickness in this part; the surgeon—therefore—cannot accurately specify the screws' position, path, diameter and length. The surgery, as a result, would not be wholly successful. Parameters for determining the position, path, diameter and length of the screws differ from one patient to another depending on the medical case and surgical diagnosis. The standard traditional tools are not efficient for all acetabular bone types, shapes, qualities and thickness in the pelvic joint.

A computer-assisted surgery pre-planning and the resulting production of patient-specific guides have solved some common problems related to traditional tools. However, still there is difficulty in specifying the positions, lengths, diameters and paths of the pelvic joint acetabulum. Present guides give only information about the central opening (the middle screw opening) of the pelvic joint acetabulum. Their design does not allow the surgeon to specify the place and status of the guide on the cotyloid cavity for being composed of three fixation cylinders with small surface areas that do not completely cover the bone surface. The cylinders are connected to a spaced central cylinder through arms. Hence, it is not possible to accurately determine the correct path of the drilling rig that makes screw paths. It is also difficult to specify the deviation of the rig's path from the correct one.

The present invention provides a patient-specific guide for fixing the pelvic joint acetabulum for patients undergoing pelvic joint replacement surgery. The guide consists of two parts: one for the pubic part and the one for the ischial part of the pelvic joint's cotyloid cavity. It is designed to correct defects of the acetabulum and guides surgeons to the optimal places for fixing the artificial joint screws, specifying their diameters and lengths according to the case and the pelvic bone status. The internal guide surface is an imprint of the pelvic bone. Hence, it is accurately fixed on the bone according to its anatomy and the vivid markers on the pelvic bone surface. This is advantageous in complicated cases in particular, such as bone corrosion, fractures and tumors.

DETAILED DESCRIPTION OF THE INVENTION

The present invention provides a patient-specific guide for mounting an artificial pelvic joint. The guide consists of two parts for making paths for fastening screws of the pelvic joint acetabulum: one for making the pubic part's screw paths of the acetabulum cavity (the upper part), and one for making the ischial part's screw paths of the acetabulum cavity (the lower part). The guide takes the shape of an evacuated hemi-sphere; each part includes four openings for its fixation on the upper surface of the cotyloid cavity, in addition to fastening and alignment arms on the surface of the bottom cavity. The template's internal surface has a topology identical to the anatomical structure of the acetabular hole. See FIGS. 1, 2, 3 & 4.

The guide is designed for correcting pelvic defects depending on a design premade by the finite element method. It determines the quality and density of the bone and guides surgeons to the optimal places for fixing artificial joint screws and specifying their diameters and lengths in accordance to the medical case and pelvic bone status. The internal guide's surface is an imprint of the pelvic bone. Hence, it is accurately fixed on the bone according to its anatomy and the vivid markers on the pelvic bone surface. This is advantageous in complicated cases in particular, such as bone corrosion, fractures and tumors. Tomography scan pictures are used for designing a three-dimensional model for the pelvic bone. Hence, the finite element method as well as the computer-assisted surgery preplanning is applied for stress analysis.

Surgical preplanning depends on the quality and thickness of the pelvic joint acetabulum cavity, the degree of bone corrosion and the presence of former fractures. Places, paths, diameters and lengths of fastening screws of the pelvic joint acetabulum are specified by considering the mechanical and anatomical axes.

The guide consists of two parts, one for making the upper part's screw paths, and one for making the lower part's screw paths of the pelvic joint acetabulum. The guide takes the shape of an evacuated semi-sphere; each part contains four openings for its fixation on the upper surface of the acetabulum cavity (see FIGS. 1 & 2).

The pubic part of the guide contains two arms for fixation and alignment on the acetabular bone. However, fixation and alignment arms are connected as a whole circuit in the ischial part of the guide.

The pubic part of the guide contains five openings for specifying the position, path, diameter and length of the fastening screws for the thigh joint acetabulum. The ischial part, however, contains three openings for specifying the position, path, diameter and length of the fastening screws for the thigh joint acetabulum. In both cases, the angles, spaces and inclinations between these eight openings are identical to those of the pelvic joint acetabulum—that is to be fixed—in accordance to the manufacturer's instructions. The surgeon will, therefore, be able to determine the position, path, diameter and length of the fastening screws of the pelvic joint acetabulum before surgery. He will also manage to determine the quality, density and thickness of the bone in the place of joint fixation (FIGS. 1 & 2).

The internal surface of both the pubic and the ischial parts has surface topology that matches that of the acetabular bone cavity for ease of fixation. The topology of the internal template surface is identical to the anatomical structure of the acetabular hole, making it an anatomical guide and distinct marker for guide fixation on the bone surface. This internal surface, whose area covers more than half of the surface area of the acetabular bone cavity, prevents the template's motion or rotation. Hence, it becomes easier for the surgeon to fix the guide in a specific position on the bone, being a patient-specific template that matches the anatomical shape of the bone scanned by tomography scan (FIGS. 5 & 6).

Previous electronic guides have a design based only on three fixation cylinders with small surface areas that do not cover the complete bone surface. The cylinders are connected to a spaced central cylinder through arms. Hence, it is not possible to accurately determine the correct path of the drilling rig that makes screw paths. It is also difficult to specify the deviation of the rig's path from the correct one.

The inventive guide solves these traditional problems by fixing the guide on the bone using two elements. The first one is fastening openings above the guide's pubic and ischial parts on the upper border of the acetabular bone. This border is considered a distinct anatomical marker easy to be recognized by the surgeon. It imparts stiffness and steadiness to the guide on the bone surface. The second element used in fixation is the internal guide surface, with both pubic and ischial parts, whose topology matches the topology of the external surface of the acetabular bone cavity. It is rested on the acetabular hole which is an anatomical guide and distinct marker for guide fixation on the bone surface. The internal guide surface ensures the fixation of the template in its desired position without the possibility of displacement or rotation. The surgeon, hence, can accurately specify the places, paths, diameters and lengths of fastening screws in the pelvic bone's acetabulum (see FIGS. 3 & 4). The complete resting of the internal guide's surface on the acetabular bone cavity prevents the drilling dig deviation from its pre-determined path. In the prior art, however, the arms between the path allocation opening and the fastening openings do not protect against the dig's deviation into a wrong path.

Surgical preplanning depends on inputting data taken from the patient's tomography scan into the concerned program. Tomography scan gives a vivid image of the bone alone without cartilages or soft tissues. In addition, tomography scan gives the same image per patient unlike resonance that gives different images by time due to the change of cartilage status and its erosion percentage. The inputted data is then converted into a three-dimensional model for the acetabular bone. Surgery pre-planning is performed as above-mentioned depending on the anatomical axes and markers for the pelvic joint.

Surgical preplanning overcomes a prior art problem: the disability to specify the quality, thickness and density of the acetabular bone, and hence determining the positions, paths, diameters and lengths of fastening screws of the pelvic joint's acetabular bone without contacting areas of low bone quality and thickness. The prior art guide cannot specify the quality, thickness and density of the bone; a fact that threatens surgery success.

The program searches for an electronic form for the guide according to the positions, paths, diameters and lengths of the fastening screws of the pelvic joint's acetabular part. The guide's internal surfaces are identical to the bone's external surface for accurate fixation.

The electronic template file is sent to a three-dimensional printer to be manufactured using nylon, a medical material approved by American Food and Drug Administration (FDA). The template is then used in performing pelvic joint fixation surgery.

On each guide, there is an imprinted code on the guide's body including data about the joint size and direction (right or left one) and the patient's name to avoid guides mingling.

The inventive guide is easy to sterilize, easy to carry and handle for its light weight. It does not exceed 50 gram, unlike traditional devices that exceed 50 kilograms in weight and consists of many boxes making them difficult to carry and sterilize.

Usability Method

The invention relates to a patient-specific guide for fixing the acetabulum of the pelvic joint for patients undergoing hip joint replacement. The guide consists of two parts: one for the pubic part and one for the ischial part of the pelvic joint's cotyloid cavity. It is used for specifying the position, path, diameter and length of fastening screws for the hip joint acetabulum. It is used for complicated cases, such as bone loss and corrosion as well as fractures and tumors. The template is manufactured using three-dimensional printers. It fits one patient only for being designed according to the concerned patient's tomography scan.

Surgeons use the inventive guide in performing surgeries for fixing artificial pelvic joints.

Figure 1:
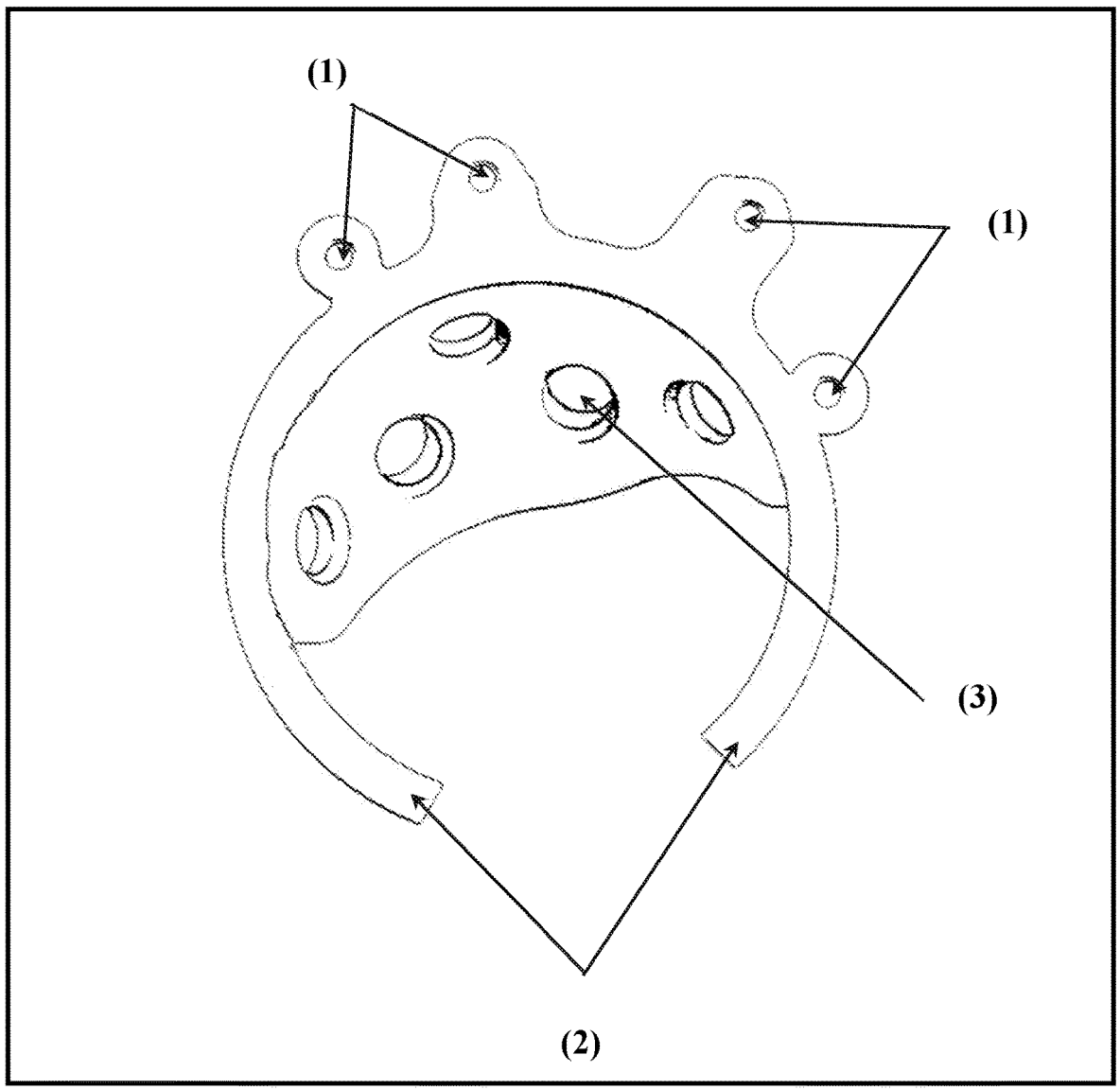
FIG. 1 represents a two-dimensional plan view for the pubic part of the guide specific for patients undergoing surgery of artificial hip joint fixation. It shows fastening openings (1), openings for determining fastening screw paths for the hip joint acetabulum (3) and fixation and alignment arms on the pubic part of the acetabular bone (2).
Figure 2:
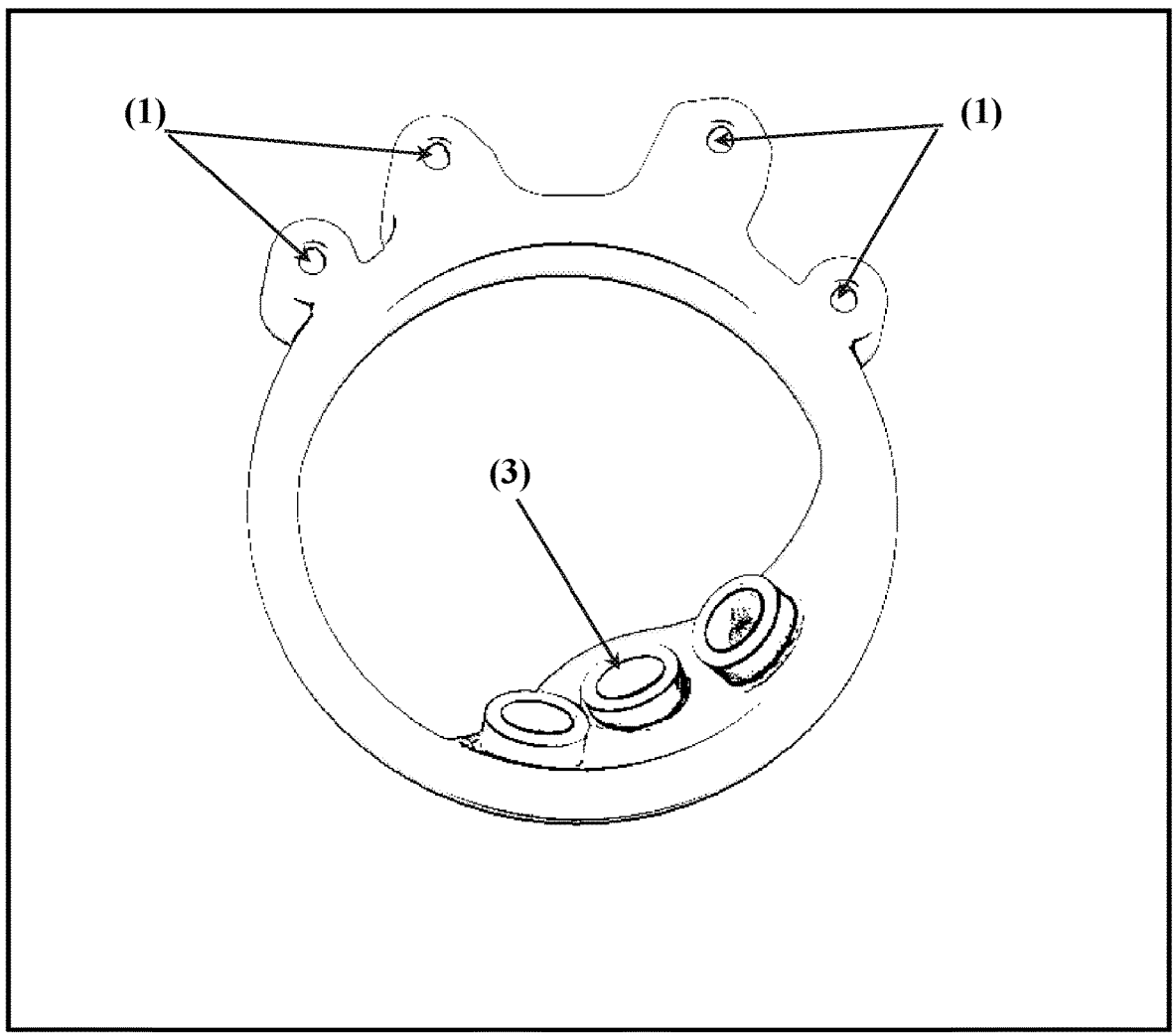
FIG. 2 represents a two-dimensional plan view for the ischial part of the guide specific for patients undergoing surgery of artificial hip joint fixation. It shows fastening openings (1), openings for determining fastening screw paths for the hip joint acetabulum (3).
Figure 3:
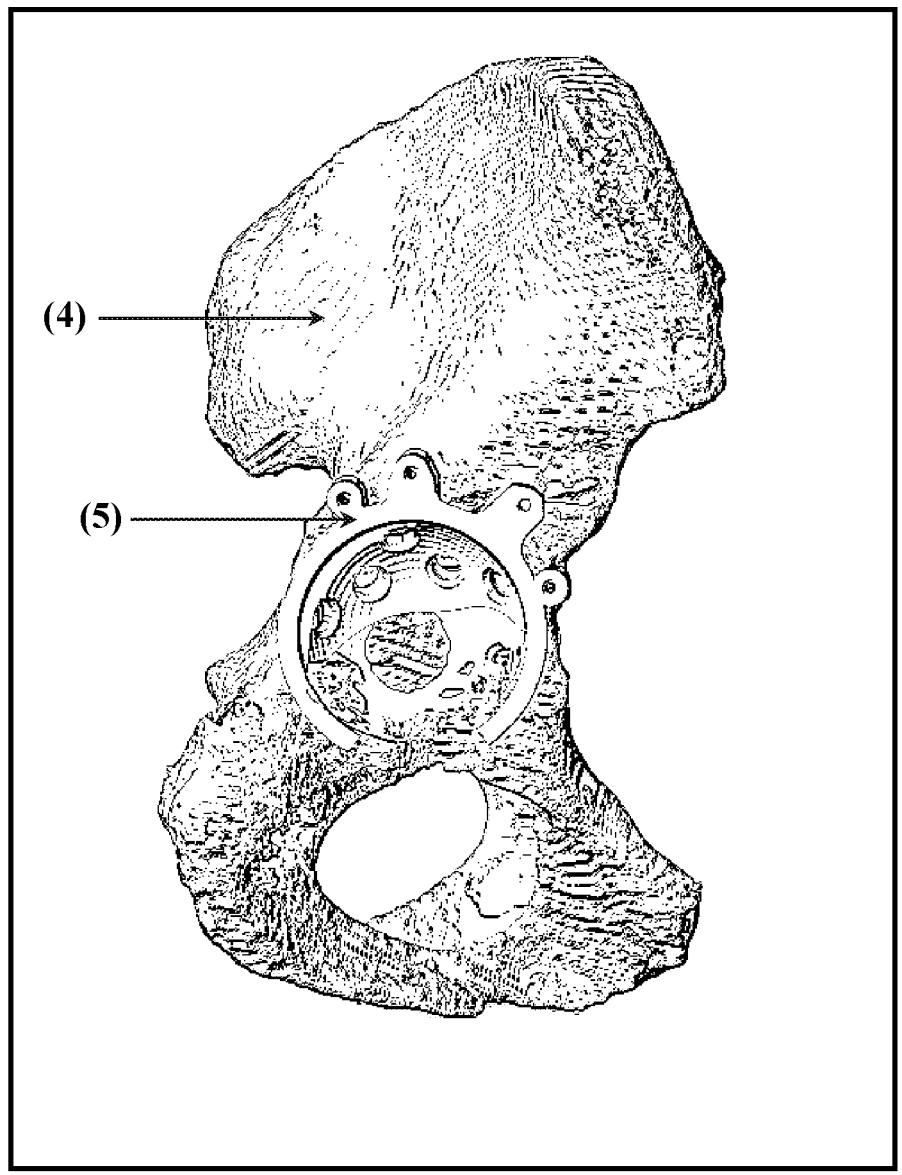
FIG. 3 represents a two-dimensional side elevation for the pubic part of the guide specific for patients undergoing surgery of artificial hip joint fixation (5). It appears in its proper place on the acetabular bone (4).
Figure 4:
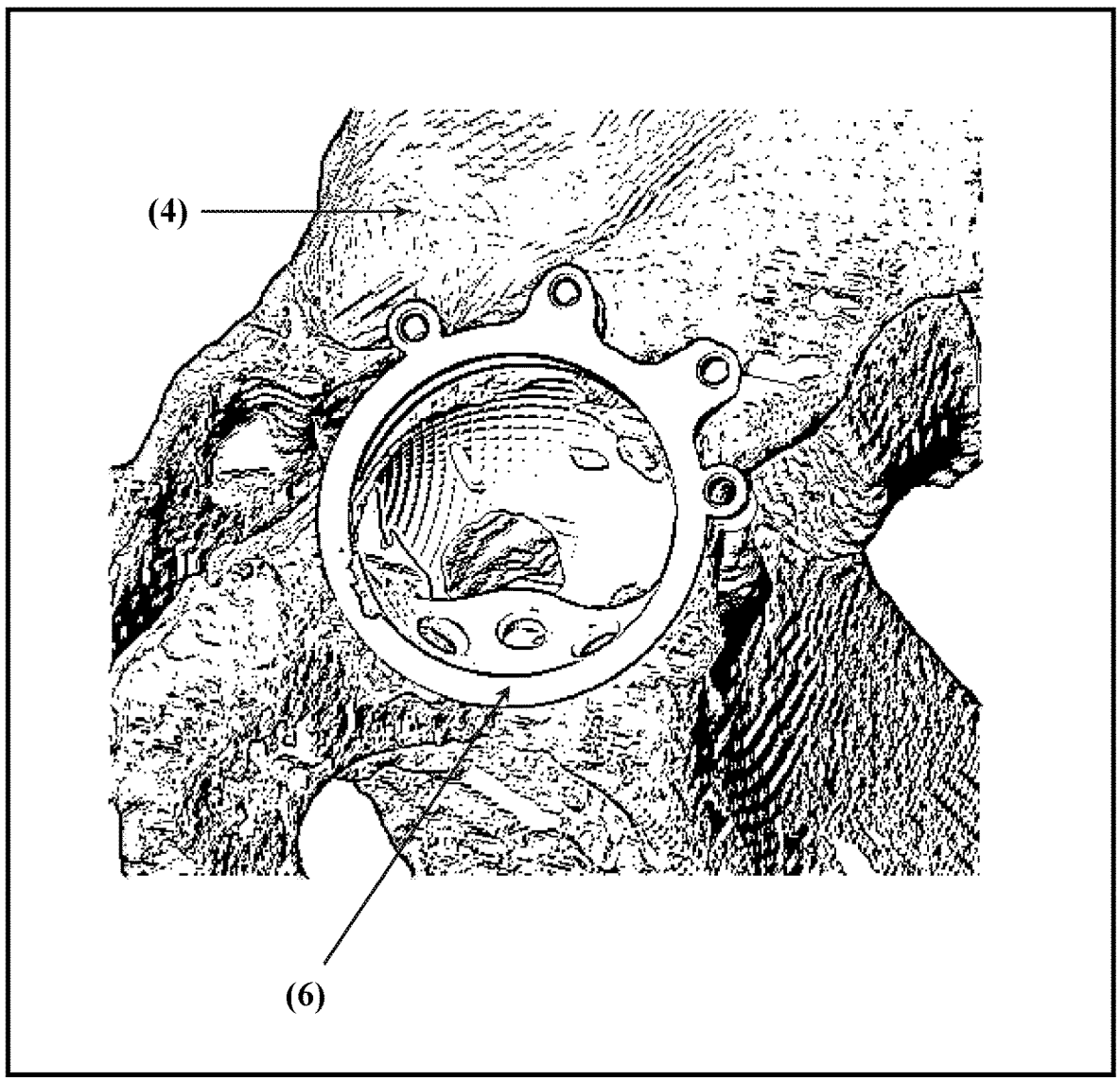
FIG. 4 represents a two-dimensional side elevation for the ischial part of the guide specific for patients undergoing surgery of artificial hip joint fixation (5). It appears in its proper place on the acetabular bone (4).
Figure 5:
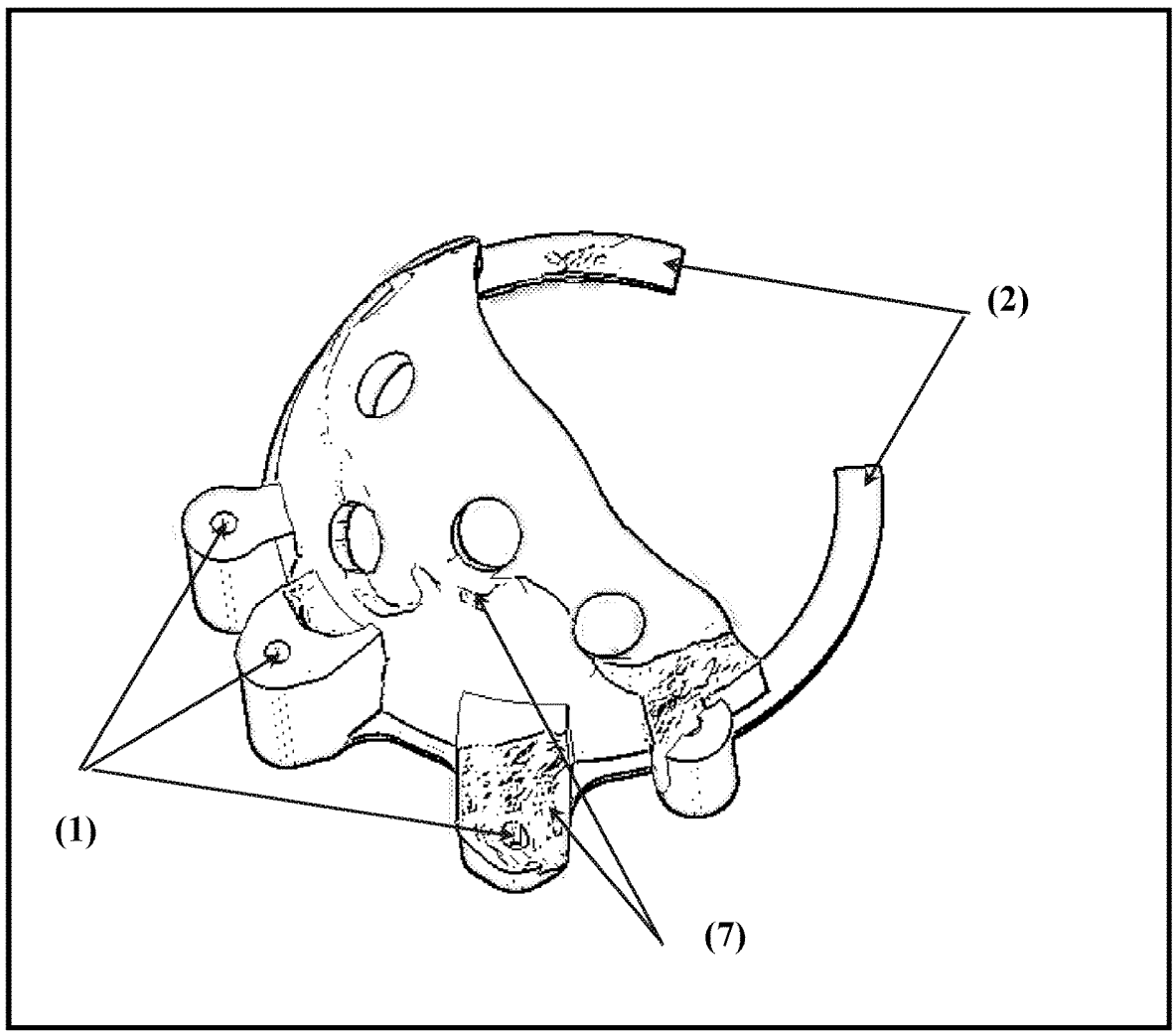
FIG. 5 represents a three-dimensional back perspective view for the pubic part of the guide specific for patients undergoing surgery of artificial hip joint fixation. The anatomical topology (7) of the guide's back surface appears in the figure which matches that of the acetabular bone's surface at its fixation place.
Figure 6:
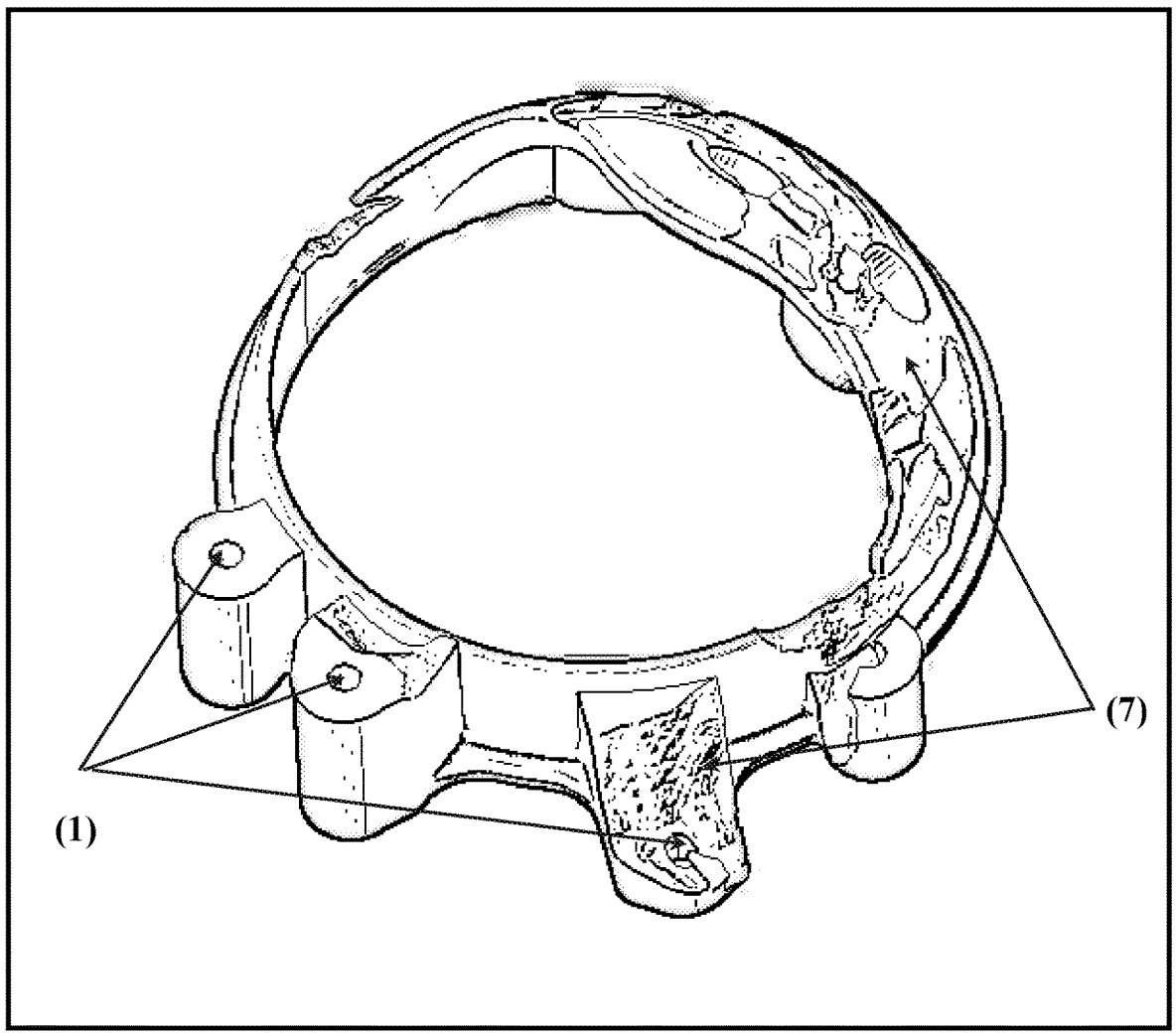
FIG. 6 represents a three-dimensional back perspective view for the ischial part of the guide specific for patients undergoing surgery of artificial hip joint fixation. The anatomical topology (7) of the guide's back surface appears in the figure which matches that of the acetabular bone's surface at its fixation place.

The invention claimed is:

1. A patient-specific guide for fixing an artificial pelvic joint for patients undergoing hip joint replacement and having a cotyloid cavity, comprising:

a first single monolithic part having a first internal surface adapted to match a pubic part of the cotyloid cavity, the first internal surface of the first part including first openings adapted for receiving first fasteners; and a second single monolithic part separate from the first part, the second part having a second internal surface adapted to match an ischial part of the cotyloid cavity, the second internal surface of the second part including second openings adapted for receiving second fasteners;

wherein the first part includes five openings adapted for specifying a position, path, and diameter of the first fasteners for fastening to an acetabulum, and the second part includes three openings adapted for specifying a position, path, and diameter of the second fasteners for fastening to the acetabulum.

2. The patient-specific guide according to claim 1, wherein the first part includes four peripheral openings adapted for receiving fasteners and the second part includes four peripheral openings adapted for receiving fasteners.

3. The patient-specific guide according to claim 2, wherein the peripheral openings of the first part correspond in location to the peripheral second openings of the second part.

4. The patient-specific guide according to claim 1, wherein the first part includes a pair of curved fastening arms having opposed ends.

5. The patient-specific guide according to claim 1, wherein the first internal surface is spherical.

6. The patient-specific guide according to claim 1, wherein the second internal surface is spherical.

7. A patient-specific guide for fixing an artificial pelvic joint for patients undergoing hip joint replacement and having a cotyloid cavity, comprising:

a single monolithic first part having a first internal surface adapted to be identical in shape to a pubic part of the cotyloid cavity, the first part including first openings adapted for receiving first fasteners; and a single monolithic second part separate from the first part, the second part having a second internal surface adapted to be identical in shape to an ischial part of the cotyloid cavity, the second part further including second openings adapted for receiving second fasteners;

wherein the first internal surface of the first part includes five openings adapted for specifying a position, path, and diameter of the first fasteners for fastening to an acetabulum, and the second internal surface of the second part includes three openings adapted for specifying a position, path, and diameter of the second fasteners for fastening to the acetabulum.

8. The patient-specific guide according to claim 7, wherein the first part includes four first openings adapted for receiving fasteners and the second part includes four second openings adapted for receiving fasteners.

9. The patient-specific guide according to claim 7, wherein the first internal surface is spherical and includes the first openings.

10. The patient-specific guide according to claim 7, wherein the second internal surface is spherical and includes the second openings.

11. The patient-specific guide according to claim 7, wherein the first openings of the first part correspond in location to the second openings of the second part.

12. A patient-specific guide for fixing an artificial pelvic joint for patients undergoing hip joint replacement and having a cotyloid cavity, comprising:

a single monolithic first part having a first internal surface adapted to correspond to the cotyloid cavity, the first part including first openings adapted for receiving first fasteners; and a single monolithic second part having a second internal surface adapted to correspond to an ischial part of the cotyloid cavity, the second part including second openings adapted for receiving second fasteners;

wherein the first openings of the first part correspond in location to the second openings of the second part;

wherein the first part includes five openings adapted for specifying a position, path, and diameter of the first fasteners for fastening to an acetabulum, and the second part includes three openings adapted for specifying a position, path, and diameter of the second fasteners for fastening to the acetabulum.

13. The patient-specific guide according to claim 12, wherein the first part includes four first openings adapted for receiving fasteners and the second part includes four second openings adapted for receiving fasteners.

14. The patient-specific guide according to claim 12, wherein the first part further includes a pair of curved fastening arms having opposed ends.

15. The patient-specific guide according to claim 12, wherein the first internal surface is spherical and includes the first openings.

16. The patient-specific guide according to claim 12, wherein the second internal surface is spherical and includes the second openings.

17. A patient-specific guide for fixing an artificial pelvic joint for patients undergoing hip joint replacement and having a cotyloid cavity, comprising:

a first single monolithic part having a first internal surface adapted to match a pubic part of the cotyloid cavity, the first internal surface of the first part including first openings adapted for receiving first fasteners; and a second single monolithic part separate from the first part, the second part having a second internal surface adapted to match an ischial part of the cotyloid cavity, the second internal surface of the second part including second openings adapted for receiving second fasteners;

wherein the first part includes four peripheral openings adapted for receiving fasteners and the second part includes four peripheral openings adapted for receiving fasteners.

18. The patient-specific guide according to claim 17, wherein the peripheral openings of the first part correspond in location to the peripheral second openings of the second part.

* * * * *